April 30, 1940. G. DE RUITER Plant Pat. 381
ROSE PLANT
Filed Aug. 28, 1939
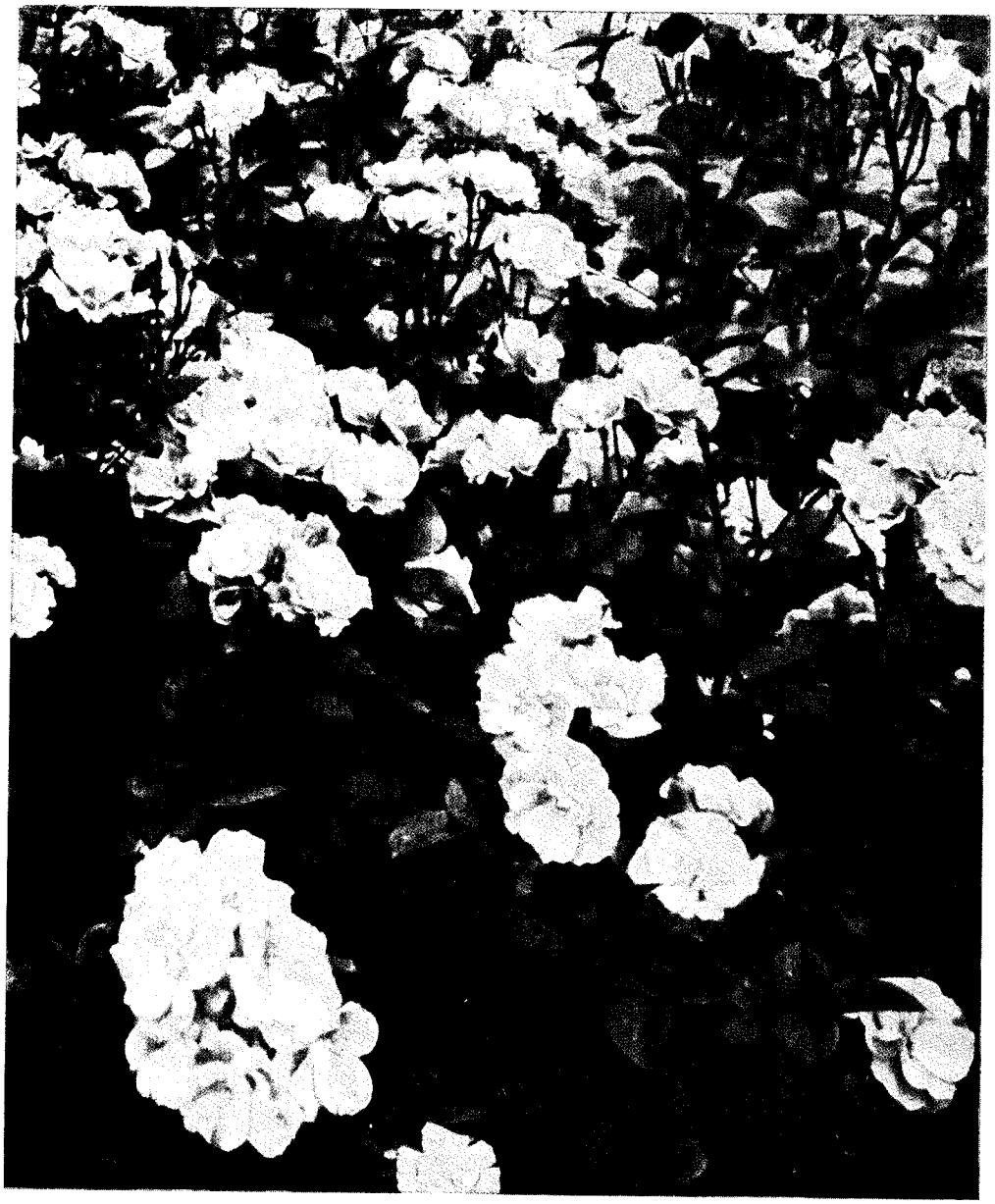
Inventor:
Gerrit de Ruiter
By Robbs & Robb
Attorneys Patented Apr. 30, 1940

Plant Pat. 381

UNITED STATES PATENT OFFICE

381

ROSE PLANT

Gerrit De Ruiter, Hazerswoude, Dorp, Netherlands, assignor to Jackson & Perkins Company, Newark, N. Y.

Application August 28, 1939, Serial No. 292,354

1 Claim. (Cl. 47—61)

This discovery relates to a new and distinct variety of rose plant, a bud sport of Else Poulsen, originating on a plant in my possession and differing therefrom in a number of important particulars.

The primary characteristic which seems to mark its distinction with reference to its parent is the color of the flowers, it being a much deeper shade than that of the buds and flowers of Else Poulsen.

As the flower ages it still retains a clear color, the petals eventually dropping off cleanly, while the flowers of the parent plant become mottled and unsightly as they age. Further this sport ordinarily carries more petals than the parent and the flowers are longer lasting.

The growth also differs from the parent plant in that it is more compact but it is just as vigorous.

All of the foregoing features of novelty evidence the fact that the sport is a decided improvement over the parent variety. A sexual reproduction of the new variety shows that these features have become established.

The following is a detail description of this new variety, the color terminology being in accordance with Ridgway's Color Standard.

Parentage: Sport.

*Parent.*—Else Poulsen.

Classification:

*Botanic.*—Large flowered polyantha.

*Commercial.*—Floribunda.

*Flower*

(Observations made at Newark, New York, in the morning of June 30, 1938.)

Blooming habit: Recurrent—continuous.

Bud:

*Size.*—Small.

*Form.*—Short with flat top. Is not affected by wet or hot weather.

*Color.*—When sepals first divide—Pomegranate Purple, Plate 12. When petals begin to unfurl—Rose Red, Plate 12. When half blown: inside of petals—Begonia Rose, Plate 1, to Rose Red, Plate 12; reverse of petals—Rose Red, Plate 12.

*Sepals.*—Branched; stand up.

*Calyx.*—Shape—pear. Size—small. Aspect—smooth.

*Peduncle.*—Length — long. Aspect—prickly. Color—Cress Green, Plate 31. Strength—erect, slender.

*Opening.*—Bud opens well. Is not affected by adverse conditions.

Bloom:

*Size.*—Small. Average size when fully expanded 2½″.

*Borne.*—In clusters, flat.

*Stems.*—Long, strong.

*Form.*—When first open—cupped. Permanence—flattens.

*Petalage.*—Semi-single (two rows of petals). Number of petals under normal conditions, 14.

*Color.*—Center of flower — Begonia Rose, Plate 1. Outer petals—Begonia Rose, Plate 1. Base of petals (aiglet)—Picric Yellow, Plate 4. Inside of petals—Begonia Rose, Plate 1, to Rose Doree, Plate 1. Reverse of petals—Pomegranate Purple, Plate 12, to Rose Red, Plate 12. General tonality from a distance—Pink.

*Discoloration.*—General tonality at end of first day—Begonia Red, Plate 1. Second day—Begonia Rose, Plate 1. Third day—Begonia Rose, Plate 1.

Petals:

*Texture.*—Thick. Is not affected by wet or hot weather.

*Appearance.* — Inside — velvety. Outside—shiny.

*Form.*—Scalloped and heart shaped.

*Arrangement.*—Imbricated (regularly arranged shinglelike). Petaloids in center, none.

*Persistence.*—Drop off cleanly.

*Fragrance.*—Slight. Nature—Sweet Briar.

*Lasting quality.*—On the plant and as cut flower, very long.

Genital organs:

*Stamens, anthers.*—Small, many. Color—Amber Yellow, Plate 16. Arrangement—regular around styles.

*Stamens, filaments (threads).*—Long. Color—Massicot Yellow, Plate 16.

*Pollen.*—Amber Yellow, Plate 16.

*Styles.*—Bunched, even; short, thin.

*Stigmas.*—Straw Yellow, Plate 16.

*Ovaries.*—All enclosed in calyx.

*Plant*

Form: Bush.
Growth: Vigorous, branching.
Foliage: 5 to 7 leaflets.
*Size.*—Medium.
*Quantity.*—Abundant.
*Color.*—New foliage: upper side, edges—Van Dyke Red, Plate 13; center—Forest Green, Plate 17; under side, edges—Van Dyke Red, Plate 13; center—Bice Green, Plate 17. Old foliage: upper side—Dark Cress Green, Plate 31; under side—Cress Green, Plate 31.
*Shape.*—Oval pointed.
*Texture.*—Upper side—glossy. Under side—smooth. Ribs and veins—prominent.
*Edge.*—Serrated (saw toothed).
*Serration.*—Single; small.
*Rachis.*—Color—Cress Green, Plate 31. Under side—smooth.
*Stipules.*—Medium length, bearded.
*Disease resistance.*—Resistant.

Wood:
*New wood.*—Color—Van Dyke Red, Plate 13. Bark—smooth.
*Old wood.*—Color—Cress Green, Plate 31. Bark—smooth.

Thorns (thorns are divided into thorns, prickles, and short needles):
*Thorns.*—Quantity: On main stalks from base—few; on laterals from stalk—none. Form—narrow base; short; hooked downward. Color when young—Madder Brown, Plate 13. Position—irregular.

I claim:

A new and distinct variety of polyantha rose plant, characterized as to novelty by its vigorous and compact growth, the depth of color of its buds and flowers and the persistence of the coloring as the flowers age, the number of petals and long lasting quality of the flowers, substantially as shown and described.

G. DE RUITER.